US012112403B2

(12) United States Patent
Ong et al.

(10) Patent No.: US 12,112,403 B2
(45) Date of Patent: Oct. 8, 2024

(54) MEDICAL IMAGE DISPLAY APPARATUS AND MEDICAL IMAGE DISPLAY SYSTEM

(71) Applicant: CANON MEDICAL SYSTEMS CORPORATION, Otawara (JP)

(72) Inventors: Guang Yi Ong, Nasushiobara (JP); Hideaki Ishii, Nasushiobara (JP); Hiroshizu Morishima, Utsunomiya (JP); Junya Suzuki, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 18/054,977

(22) Filed: Nov. 14, 2022

(65) Prior Publication Data
US 2023/0154061 A1 May 18, 2023

(30) Foreign Application Priority Data
Nov. 16, 2021 (JP) .................................. 2021-186636

(51) Int. Cl.
G06T 11/00 (2006.01)
G06F 3/0354 (2013.01)
G06F 3/0482 (2013.01)

(52) U.S. Cl.
CPC .......... *G06T 11/00* (2013.01); *G06F 3/03543* (2013.01); *G06F 3/0482* (2013.01); *G06T 2200/24* (2013.01); *G06T 2210/41* (2013.01)

(58) Field of Classification Search
CPC ............. G06F 3/03543; G06F 3/04812; G06F 3/0482; G06F 3/04845; G06F 2203/04803; G06T 11/00; G06T 2200/24; G06T 2210/41; G16H 30/40; G16H 40/63; G16H 50/20
See application file for complete search history.

(56) References Cited

U.S. PATENT DOCUMENTS 10,127,662 B1 * 11/2018 Reicher ...................... G06T 7/30
10,929,508 B2 * 2/2021 Reicher .................. G16H 30/40
2009/0225102 A1 * 9/2009 Okubo ..................... G06F 16/58
345/661

FOREIGN PATENT DOCUMENTS

JP    2010-88709 A    4/2010

* cited by examiner

Primary Examiner — Stacy Khoo
(74) Attorney, Agent, or Firm — Oblon, McClelland, Maier & Neustadt, L.L.P.

(57) ABSTRACT

The medical image display apparatus according to any of embodiments includes processing circuitry. The processing circuitry is configured to determine whether a mouse cursor is superimposed on a display range of interpretation-target medical image data in a display screen of a display or not. Further, the processing circuitry is configured to display, when the mouse cursor is determined to be superimposed on the display range, at least one choice of comparative medical image data corresponding to interpretation-target medical image data specified by the position of a mouse cursor in an interpretation adjacent region where the specified interpretation-target medical image data is not superimposed and is adjacent to the specified interpretation-target medical image data.

4 Claims, 11 Drawing Sheets

MEDICAL IMAGE DISPLAY APPARATUS AND MEDICAL IMAGE DISPLAY SYSTEM

CROSS-REFERENCE TO RELATED APPLICATION

This application is based upon and claims the benefit of priority from Japanese Patent Application No. 2021-186636, filed on Nov. 16, 2021, the entire contents of which are incorporated herein by reference.

FIELD

Disclosed embodiments relate to a medical image display apparatus and a medical image display system.

BACKGROUND

Interpretation work by a reader such as a doctor using a medical image display system includes a process of follow-up observation. In the process of the follow-up observation, it is common to simultaneously display a plurality of images side by side for comparison, for example, to parallelly display medical image data to be interpreted and image data to be compared. Conventionally, in a hospital, medical image data acquired by imaging with a medical image diagnostic apparatus are stored to establish a database. An operator searches the database for medical image data to be interpreted (hereinafter referred to as "interpretation-target image data") and choices of medical image data to be compared (hereinafter referred to as "comparative image data") by, for example, keyword search.

Specifically, the operator inputs one or more keywords in the search field (or box) based on desired attributes such as a patient ID (Identification), an examination UID (Unique Identification), a series UID, an examination site, imaging conditions, and examination time. In response to this keyword input, the medical image display system searches the database to acquire choices of the comparative image data and the interpretation-target image data corresponding to the keyword(s). Further, the medical image display system displays the choices of the comparative image data in a thumbnail field at a predetermined or default position in the upper part of the display screen, and then the operator selects desired comparative image data displayed at the default position.

DETAILED DESCRIPTION

A medical image display apparatus and a medical image display system according to any of embodiments will be described with reference to the accompanying drawings.

The medical image display apparatus according to any of embodiments includes processing circuitry. The processing circuitry is configured to determine whether a mouse cursor is superimposed on a display range of interpretation-target medical image data in a display screen of a display or not. Further, the processing circuitry is configured to display, when the mouse cursor is determined to be superimposed on the display range, at least one choice of comparative medical image data corresponding to interpretation-target medical image data specified by the position of a mouse cursor in an interpretation adjacent region where the specified interpretation-target medical image data is not superimposed and is adjacent to the specified interpretation-target medical image data.

Figure 1:
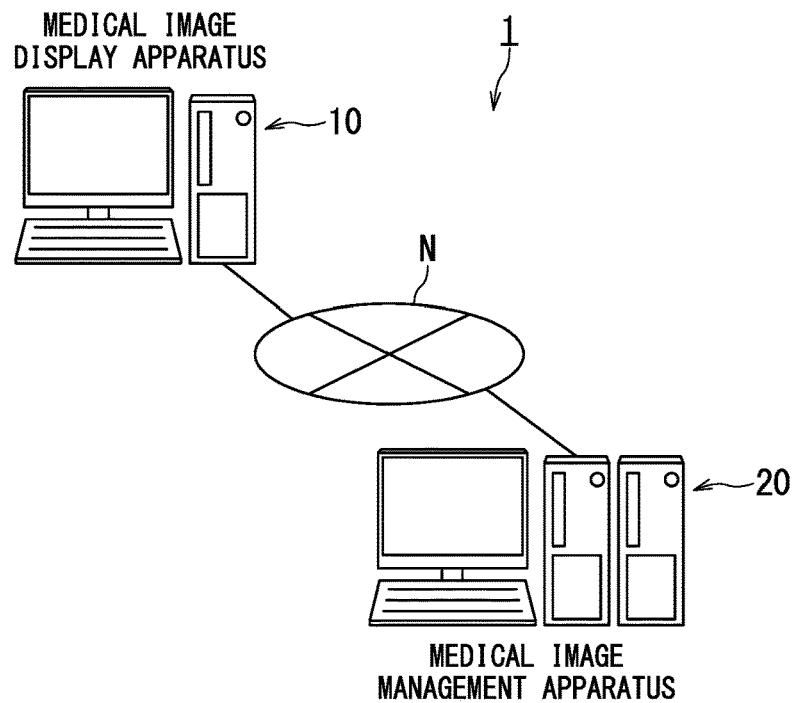
FIG. 1 is a schematic diagram illustrating a configuration of a medical image display system provided with a medical image display apparatus according to one embodiment.

FIG. 1 is a schematic diagram illustrating a configuration of a medical image display system provided with a medical image display apparatus according to one embodiment.

FIG. 1 illustrates a medical image display system 1 that includes a medical image display apparatus (which is also called an image viewer) 10 according to the present embodiment. The medical image display system 1 includes: the medical image display apparatus 10; and one or more medical image management apparatuses (which are also called image servers) 20. The medical image display apparatus 10 and each medical image management apparatus 20 are interconnected via a network N which enables communication with each other. In this interconnection, for example, an electronic connection via an electronic network can be applied. The electronic network means a general information communication network using telecommunication technology and includes a wireless/wired backbone LAN (Local Area Network) of a hospital, the Internet network, a telephone communication network, an optical fiber communication network, a cable communication network, and a satellite communication network, for example.

The medical image display system 1 stores medical image data acquired by a medical image diagnostic apparatus (not shown) as well as shared objects in a database (i.e., to establish a database by storing data and objects), and further searches and displays the medical image data in response to an operation by an operator such as a doctor. The medical image display system 1 is mainly used for interpreting (i.e., reading) images. Generally, at the time of interpreting an image, interpretation-target image data and comparative image data and/or other medical image data are displayed side by side for follow-up observation. The medical image diagnostic apparatus includes an X-ray diagnostic apparatus such as a CR (Computed Radiography) apparatus, an X-ray CT (Computed Tomography) apparatus, an MRI (Magnetic Resonance Imaging) apparatus, an ultrasonic diagnostic apparatus, and a nuclear medicine diagnostic apparatus, for example. The medical image data include CR image data acquired by a CR apparatus, CT image data acquired by an X-ray CT apparatus, MR image data acquired by an MRI apparatus, ultrasonic image data acquired by an ultrasonic diagnostic apparatus, and nuclear medicine image data acquired by a nuclear medicine diagnostic apparatus, for example. The shared objects are data that include: imaging conditions; information for identifying the medical image data acquired by imaging; and reference information for identifying the medical image data having been referred to during imaging. The shared objects are generated based on a series of data obtained by a series of imaging.

The medical image display apparatus 10 and the medical image management apparatus 20 is configured as a computer. The medical image management apparatus 20 is, for example, a DICOM (Digital Imaging and Communications in Medicine) server, and is connected to apparatuses such as the medical image display apparatus 10 via the network N such that data can be sent and received. The medical image display apparatus 10 causes the medical image management apparatus 20 to search for medical image data corresponding to a predetermined patient ID, a predetermined examination ID, and a predetermined series ID so as to retrieve the medical image data from the medical image management apparatus 20 on the basis of a so-called Query/Retrieve function.

Figure 2:
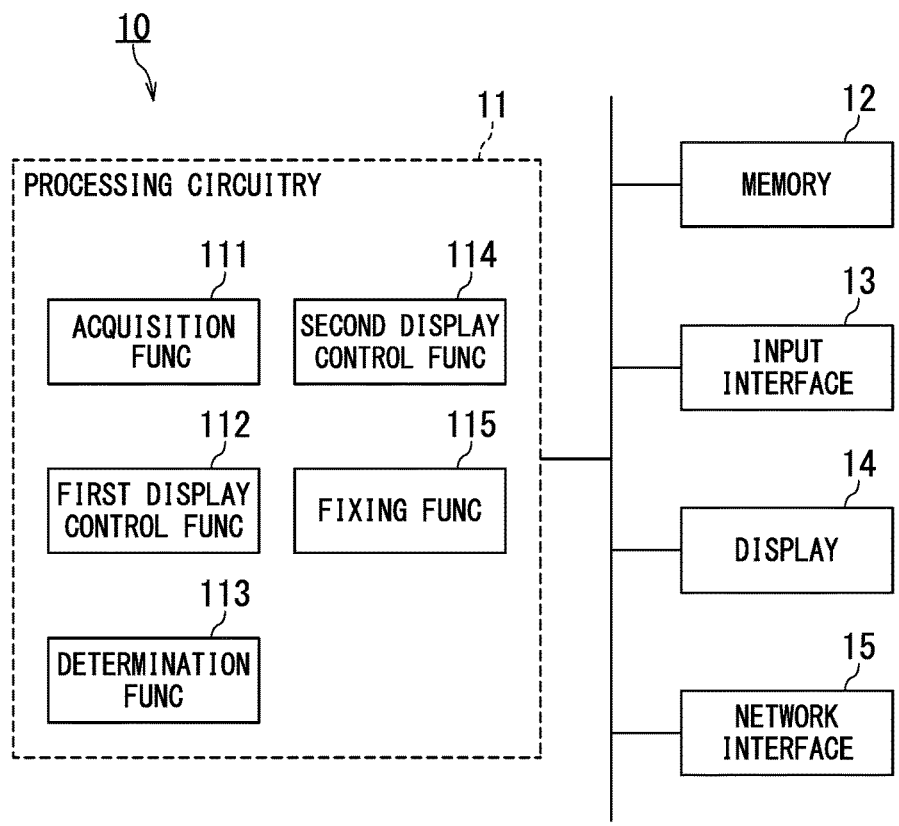
FIG. 2 is a schematic diagram illustrating the configuration and functions of the medical image display apparatus according to the embodiment.

FIG. 2 is a schematic diagram illustrating the configuration and functions of the medical image display apparatus 10.

As shown in FIG. 2, the medical image display apparatus 10 includes processing circuitry 11, a memory 12, an input interface 13, a display 14, and a network interface 15.

The processing circuitry 11 controls the operation of medical image display apparatus 10 depending on input operations by an operator via the input interface 13. The processing circuitry 11 is, for example, an ASIC (Application Specific Integrated Circuit), a programmable logic device, or a processor such as a special-purpose or general-purpose CPU (Central Processing Unit), an MPU (Micro Processor Unit), and a GPU (Graphics Processing Unit). The programmable logic device includes, for example, an SPLD (Simple Programmable Logic Device), a CPLD (Complex Programmable Logic Device), and an FPGA (Field Programmable Gate Array).

The processing circuitry 11 may be configured by a single circuit or by combination of a plurality of independent processing-circuit elements. In the latter case, the memory 12 may be provided individually for each of the processing-circuit elements or one memory 12 may store all the programs corresponding to the functions of the plurality of processing-circuit elements.

The memory 12 is composed of, for example, a hard disk, an optical disc, or a semiconductor memory element such as a RAM (Random Access Memory) and a flash memory. The memory 12 may be composed of portable media such as a USB (Universal Serial Bus) memory and a DVD (Digital Video Disk). The memory 12 stores various processing programs in the processing circuitry 11 (including not only application programs but also an OS (Operating System)) and/or data necessary for executing the programs, for example. In addition, the OS may include a GUI (Graphical User Interface) that makes extensive use of graphics when displaying information for an operator on the display 14 and allows basic operations to be performed through the input interface 13.

The input interface 13 includes: an input device that can be operated by an operator; and an input circuit to which signals from the input device are inputted. The input device is achieved by, for example, a trackball, a switch, a mouse, a keyboard, a touch pad that enables input operations by touching an operation screen, a touch screen in which a display screen and a touch pad are integrated, a non-contact input device using an optical sensor, and a voice input device. When the operator manipulates the input device, the input circuit generates a signal corresponding to the manipulation and outputs the generated signal to the processing circuitry 11. The medical image display apparatus 10 may include a touch panel in which the input device is integrated with the display 14. Additionally, the input device is not limited to a configuration having physical operation components such as a mouse and a keyboard. For example, the input interface 13 may also include a configuration in which the input circuit receives an electrical signal corresponding to an input operation from an external input device provided separately from the medical image display apparatus 10, and outputs this electrical signal to the processing circuitry 11.

The display 14 is a display device such as a liquid crystal display panel, a plasma display panel, and an organic EL (Electro Luminescence) panel. The display 14 is connected to the processing circuitry 11 and displays images and various information items generated under the control of the processing circuitry 11.

The network interface 15 is composed of connectors that conform to parallel connection specifications and/or serial connection specifications. The network interface 15 has a function of performing communication control in accordance with respective standards and connecting with the network N (FIG. 1) through a telephone network, and thereby can connect the medical image display apparatus 10 to the network N.

Similarly to the medical image display apparatus 10, the medical image management apparatus 20 includes processing circuitry, a memory, a DB (Database), an input interface, a display, and a network interface (not shown). In terms of configuration, the processing circuitry, the memory, the input interface, the display, and the network interface of the medical image management apparatus 20 are respectively equivalent to the processing circuitry 11, the memory 12, the input interface 13, the display 14, and the network interface 15 of the medical image display apparatus 10, and duplicate description is omitted. The DB of the medical image management apparatus 20 is a storage unit that stores medical image data and shared objects. The DB stores medical image data and shared objects under the control of the processing circuitry. Further, under the control of the processing circuitry of the medical image management apparatus 20, the DB provides the medical image display apparatus 10 with specific medical image data chosen from the stored medical image data by following the requests from the medical image display apparatus 10.

Figure 3:
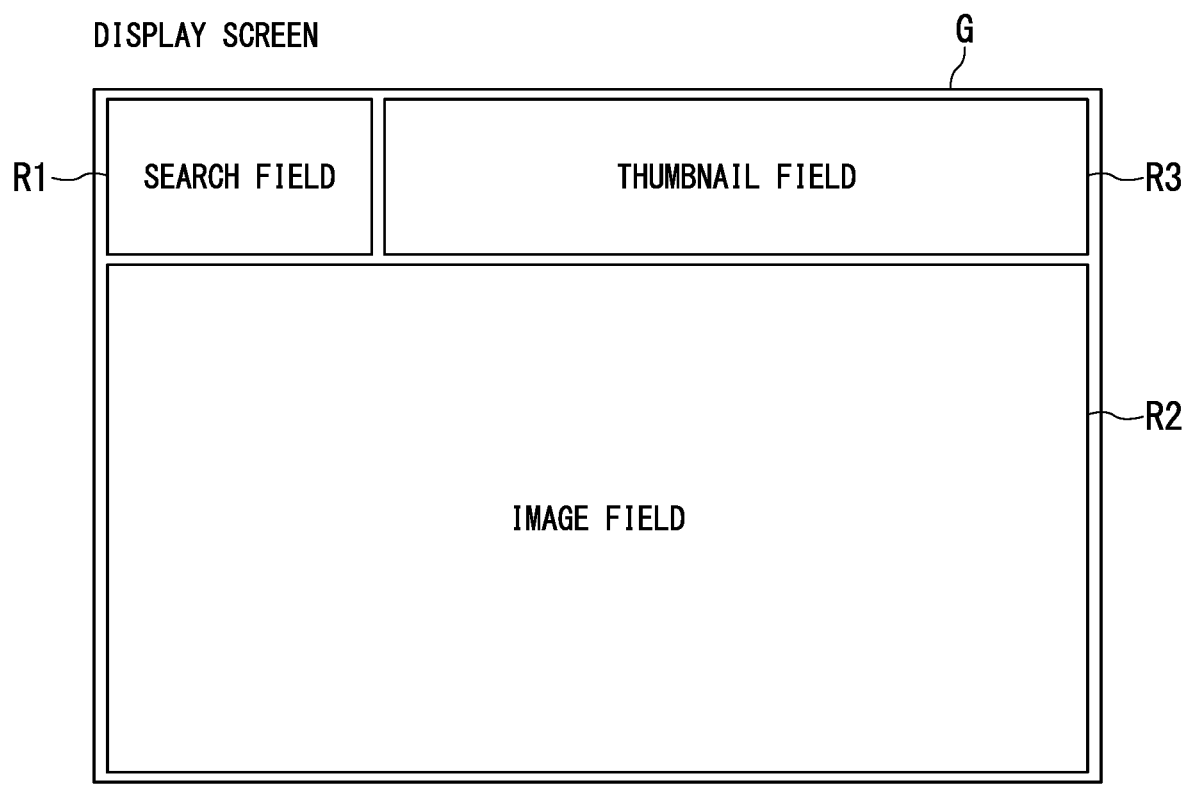
FIG. 3 is a diagram illustrating an example of layout of display screens in the medical image display apparatus according to the embodiment.

Next, functions of the medical image display apparatus 10 will be described by referring to FIG. 2 and FIG. 3. FIG. 3 is a diagram illustrating a layout of a display screen.

The processing circuitry 11 of the medical image display apparatus 10 reads out and executes the computer programs stored in the memory 12 or embedded directly in the processing circuitry 11 so as to implement an acquisition function 111, a first display control function 112, a determination function 113, a second display control function 114, and a fixing function 115. Although the functions 111 to 115 to be described below function as software by executing the computer programs, all or at least one of the functions 111 to 115 may be achieved by a circuit such as an ASIC.

The acquisition function 111 includes a function of acquiring the interpretation-target image data and choices of the comparative image data corresponding to the interpretation-target image data from the medical image management apparatus 20 via the network N. Specifically, when the operator inputs one or more keyword(s) based on the attributes of the medical image data to be acquired (such as a patient ID, an examination UID, a series UID, an examination site, imaging conditions, and examination time) in a search field (or box) R1 of a display screen G, in response to this input, the medical image display system 1 searches the DB of the medical image management apparatus 20 and acquires the medical image data corresponding to the keyword(s) as the interpretation-target image data. Additionally, the acquisition function 111 uses a specification method described below to acquire the medical image data corresponding to the interpretation-target image data as a choice of the comparative image data.

The first display control function 112 includes a function of displaying the interpretation-target image data, which are acquired from the search by the acquisition function 111, in an image field R2 of the display screen G.

The determination function 113 includes a function of determining whether or not a mouse cursor is superimposed on the display range of the interpretation-target image data displayed in the image field R2 of the display screen G of the display 14. The determination function 113 continuously detects the mouse cursor, and determines that it is superimposed when the detected mouse cursor is located in the display range of the interpretation-target image data. Additionally, the determination function 113 may continuously detect the mouse cursor, and determine that it is superimposed when (i) the detected mouse cursor is located in the display range (e.g., overlaid with a button icon within the display range) of the interpretation-target image data and (ii) a selection instruction via the input interface 13 (performed by single or double click of the mouse button or click of an icon, for example) is also received.

The second display control function 114 includes a function of displaying choices of the comparative image data corresponding to the specified interpretation-target image data in an "interpretation adjacent region" on the display screen when the determination function 113 determines that the mouse cursor is superimposed on the display range of the interpretation-target image data. The interpretation adjacent region is defined as the region where the interpretation-target image data specified by the position of the mouse cursor is not superimposed and is adjacent to the specified interpretation-target image data. The term "adjacent" includes the cases where the choices of the comparative image data displayed on the display screen may be in contact with the top, bottom, left, or right of the interpretation-target image data, may be closer to the interpretation-target image data than the medical image data in a thumbnail field R3 (FIG. 3), or may be away from the interpretation-target image data at certain distance. Additionally, the choices of the comparative image data may be displayed in the same layer as the image data on the display screen or may be displayed in a layer in front of those image data. For example, when the choices of the comparative image data are displayed in the front layer, the second display control function 114 can display the choices of the comparative image data corresponding to the interpretation-target image data in a pop-up menu (i.e., a first pop-up menu described below) displayed in the interpretation adjacent region. Hereinafter, a description will be given of the case where the second display control function 114 displays the choices of the comparative image data corresponding to the interpretation-target image data in the pop-up menu displayed in the interpretation adjacent region.

The fixing function 115 includes a function of determining (i.e., fixing) the comparative image data, as selected via the mouse cursor, from the plurality of choices of the comparative image data displayed in the first pop-up menu by the second display control function 114. In this case, the second display control function 114 displays the determined or fixed comparative image data.

Next, a method of displaying medical images in the medical image display system 1 will be described.

Figure 4:
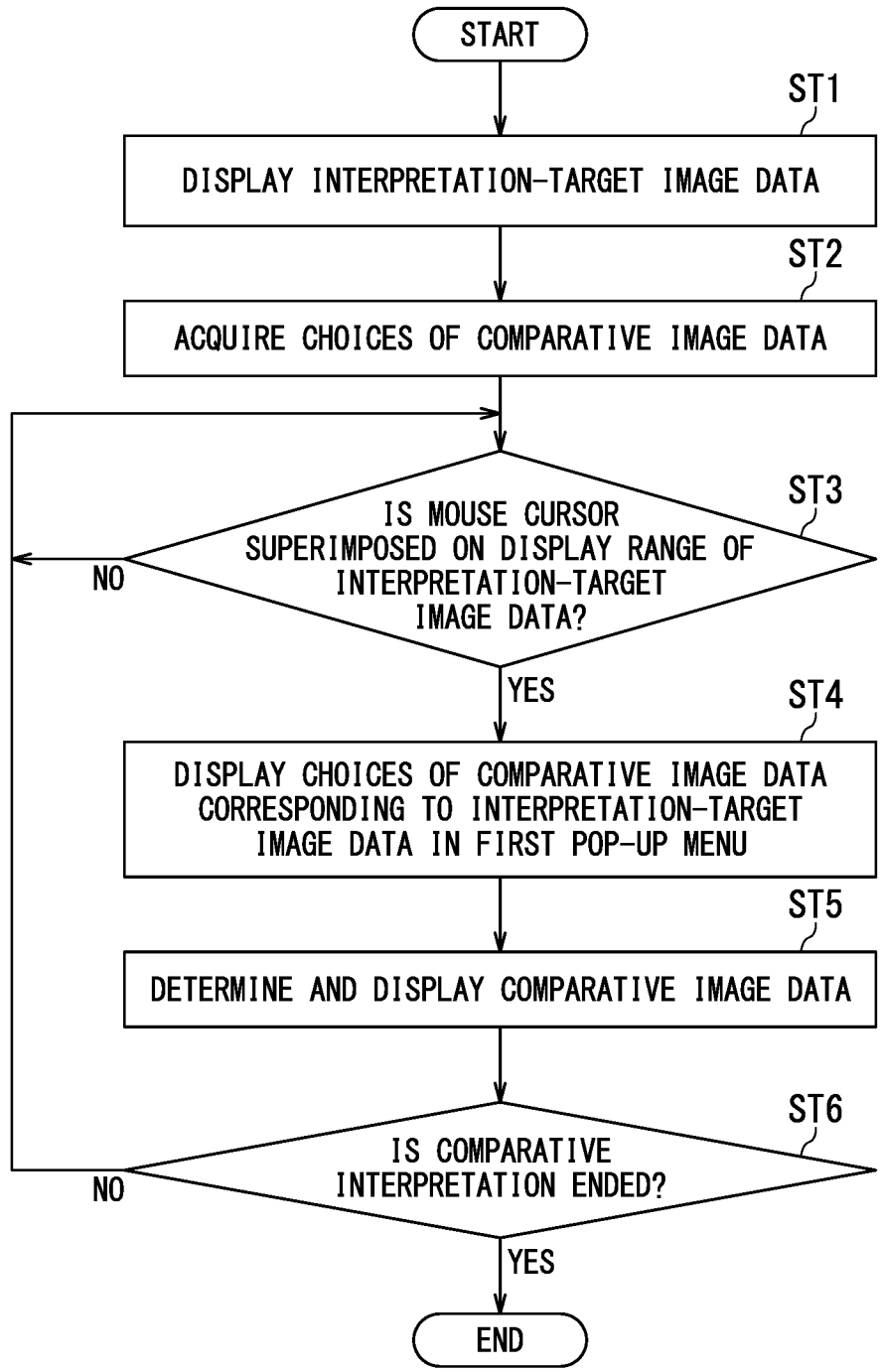
FIG. 4 is a flowchart illustrating a method of displaying medical images in a medical image display system that includes the medical image display apparatus according to the embodiment.

FIG. 4 is a flowchart illustrating a method of displaying medical images. In FIG. 4, each reference sign consisting of "ST" and number on its right side indicates each step in the flowchart.

In the step ST1, when the acquisition function 111 of the medical image display apparatus 10 acquires the interpretation-target image data from the medical image management apparatus 20 via the network N, the first display control function 112 displays the acquired interpretation-target image data in the image field R2 of the display screen G. Specifically, the operator inputs one or more keyword(s) based on the attributes of the medical image data to be acquired (for example, a patient ID, an examination UID, a series UID, an examination site, imaging conditions, and examination time) in the search field R1 of the display screen G. In response to this input, the medical image display system 1 searches the DB of the medical image management apparatus 20 and acquires the medical image data corresponding to the keyword(s) as the interpretation-target image data.

In the step ST2, the acquisition function 111 acquires choices of the comparative image data corresponding to the interpretation-target image data displayed in the step ST1. Various cases of the comparative image data corresponding to the interpretation-target image data will be described below in the section of "Method of Specifying Choices of Comparative Image Data".

In the step ST3, the determination function 113 determines whether the mouse cursor is superimposed on the display range of the interpretation-target image data in the image field R2 on the display screen G of the display 14. If the determination result of the step ST3 is NO, i.e., the mouse cursor is not superimposed on the display range of the interpretation-target image data, the determination function 113 waits until the mouse cursor is superimposed on the display range of the interpretation-target image data.

Conversely, if the determination result of the step ST3 is YES, i.e., the mouse cursor is superimposed on the display range of the interpretation-target image data, the processing proceeds to the step ST4 in which the second display control function 114 displays the choices of the comparative image data corresponding to the interpretation-target image data in the first pop-up menu shown in the interpretation adjacent region.

Figure 5:
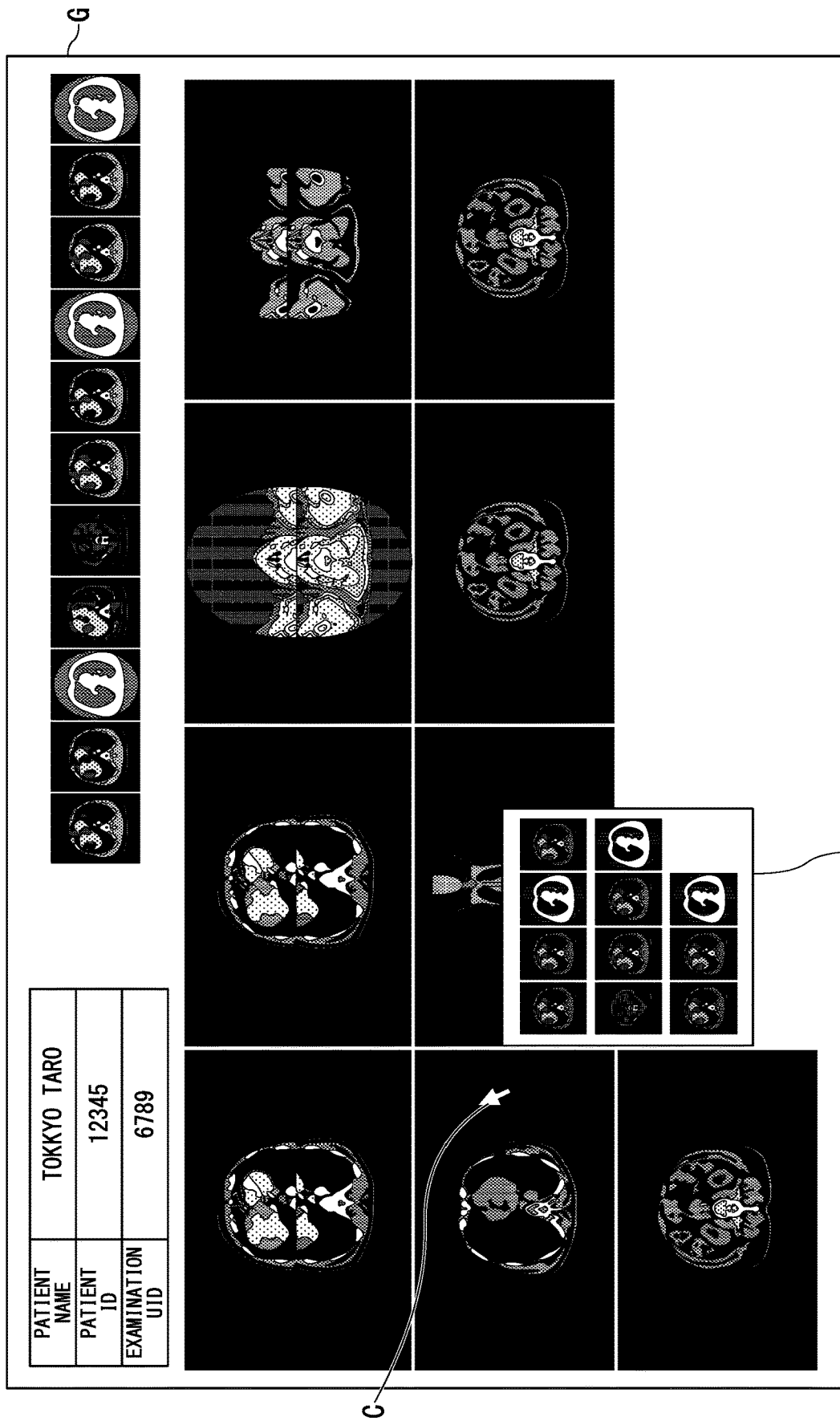
FIG. 5 is a schematic diagram illustrating a method of displaying choices of the comparative image data in the medical image display apparatus according to the embodiment.
Figure 6:
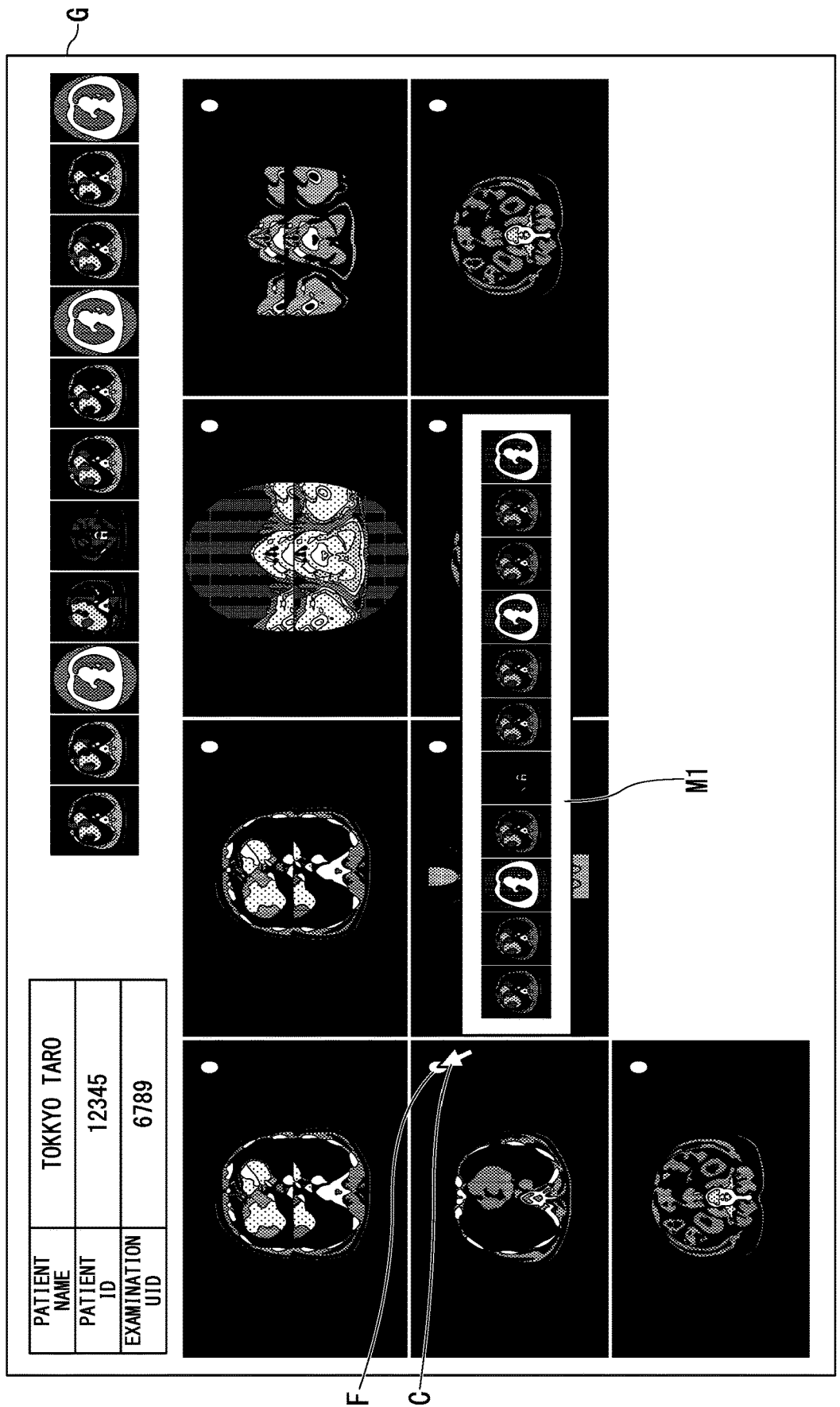
FIG. 6 is a schematic diagram illustrating a method of displaying choices of the comparative image data in the medical image display apparatus according to the embodiment.

FIG. 5 and FIG. 6 are schematic diagrams illustrating a method of displaying choices of the comparative image data in the medical image display apparatus 10 according to the present embodiment. In each of FIG. 5 and FIG. 6, the layout of the display screen G is the same as the layout of the display screen G shown in FIG. 3.

As shown in FIGS. 5 and 6, a plurality of choices of the comparative image data are displayed in the first pop-up menu M1 in the interpretation adjacent region where the interpretation-target image data (partially overlaid with the mouse cursor C) specified among the plurality of interpretation-target image data is not superimposed and is adjacent to the specified interpretation-target image data. The choices of the comparative image data in the first pop-up menu M1 is displayed at a position closer to the specified interpretation-target image data (or the mouse cursor C) than the choices of the corresponding comparative image data displayed in the thumbnail field R3. The plural choices of the comparative image data may be displayed in the shape of "U" or "L", or in rectangle around the specified interpretation-target image data on the display screen G or may be displayed so as to draw a rectangle over the top, bottom, right, and left of the image data.

The determination function 113 continuously detects the mouse cursor C on the display screen, and determines that it is superimposed when the detected mouse cursor C is located in the display range of the interpretation-target image data (FIG. 5). Additionally, the determination function 113 may continuously detect the mouse cursor and determine that it is superimposed when (i) the detected mouse cursor C is superimposed on the display range of the interpretation-target image data and (ii) a selection instruction via the input interface 13 (performed by single or double click of the mouse button or click of the icon, for example) is also received. The operator can readily select the desired comparative image data from the plurality of choices of the comparative image data displayed in the first pop-up menu M1. Further, information such as a type of the medical image diagnostic apparatus, a series UID, and a protocol name may be displayed around the respective choices of the comparative image data presented in the first pop-up menu M1.

As shown in FIG. 6, the determination function 113 may continuously detect the mouse cursor C on the display screen and determine that it is superimposed when (i) the detected mouse cursor C is overlaid with a button icon F in the display range of the interpretation-target image data and (ii) a selection instruction via the input interface 13 (performed by single or double click of the mouse button or click of the icon, for example) is also received.

Since the medical image display apparatus 10 eliminates the need to select comparative image data from the thumbnail field R3, the image display of the thumbnail field R3 in FIG. 5 and FIG. 6 can be omitted.

Figure 7:
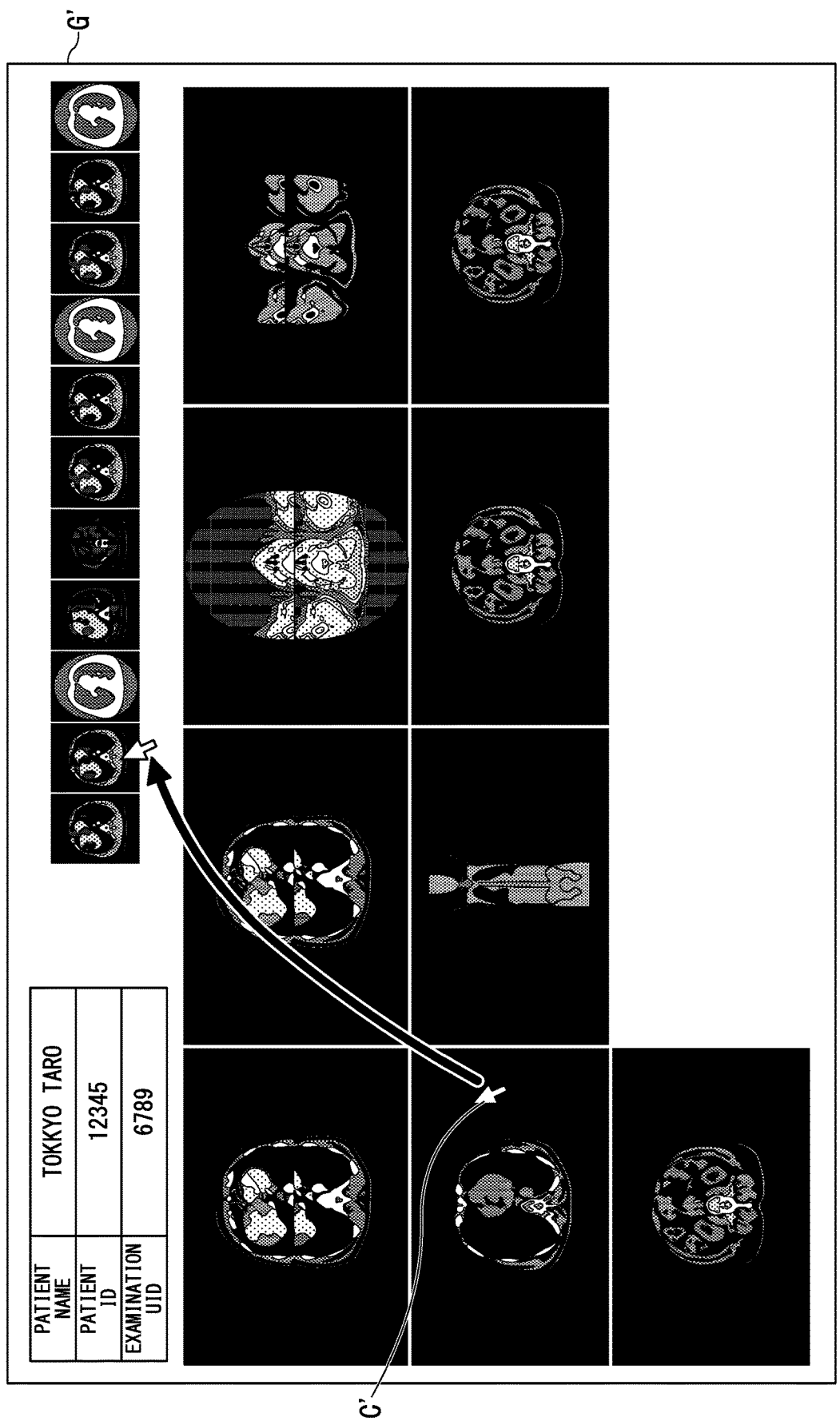
FIG. 7 is a schematic diagram illustrating a method of displaying choices of the comparative image data in a conventional medical image display apparatus.

FIG. 7 is a schematic diagram illustrating a method of displaying choices of the comparative image data in a conventional medical image display apparatus, as a comparative example with respect to the present embodiment. In FIG. 7, the layout of the display screen G' is the same as the layout of the display screen G shown in FIG. 3.

As shown in FIG. 7, in the conventional medical image display apparatus, for example, a plurality of choices of the comparative image data are displayed as thumbnails in the thumbnail field, which is the default position in the upper right row of the display screen. When trying to select predetermined comparative image data on this display screen, the operator must use the input interface 13 to move the mouse cursor C' from the lower row, where the interpretation-target image data are arranged, to the upper right thumbnail field (such movement is shown by arrow in FIG. 7). As a result, it takes time to move the mouse cursor C', and the efficiency of image interpretation decreases.

Returning to FIG. 4, in the step ST5, the fixing function 115 determines (i.e., fixes) at least one comparative image data, as selected via the mouse cursor C, among the plurality of choices of the comparative image data displayed in the first pop-up menu M1 (FIG. 5 and FIG. 6) by the second display control function 114. Further, the fixing function 115 displays the determined (i.e., fixed) comparative image data in the image field R2. Such comparative image data to be determined and displayed in the step ST5 may be one or more.

In the step ST6, the fixing function 115 determines whether to end the comparative interpretation. In other words, the fixing function 115 determines whether to change the selected interpretation-target image data in the image field R2 of the display screen G. If the determination result of the step ST6 is No, i.e., the comparative interpretation is not yet ended, the determination function 113 waits until the mouse cursor C is moved and superimposed on the display range of other interpretation-target image data.

Conversely, if the determination result of the step ST6 is YES, i.e., the comparative interpretation is ended, the medical image display system 1 ends the operation of the comparative interpretation of image data acquired in the step ST1.

According to the medical image display apparatus 10 described above, the choices of the comparative image data can be selected from the first pop-up menu shown near the interpretation-target image data, which enhances efficiency when selecting the comparative image data corresponding to the interpretation-target image data.

First Modification

The second display control function 114 can also display choices of the display layout in the pop-up menu (i.e., second pop-up menu described below) that is displayed in the interpretation adjacent region.

Figure 8:
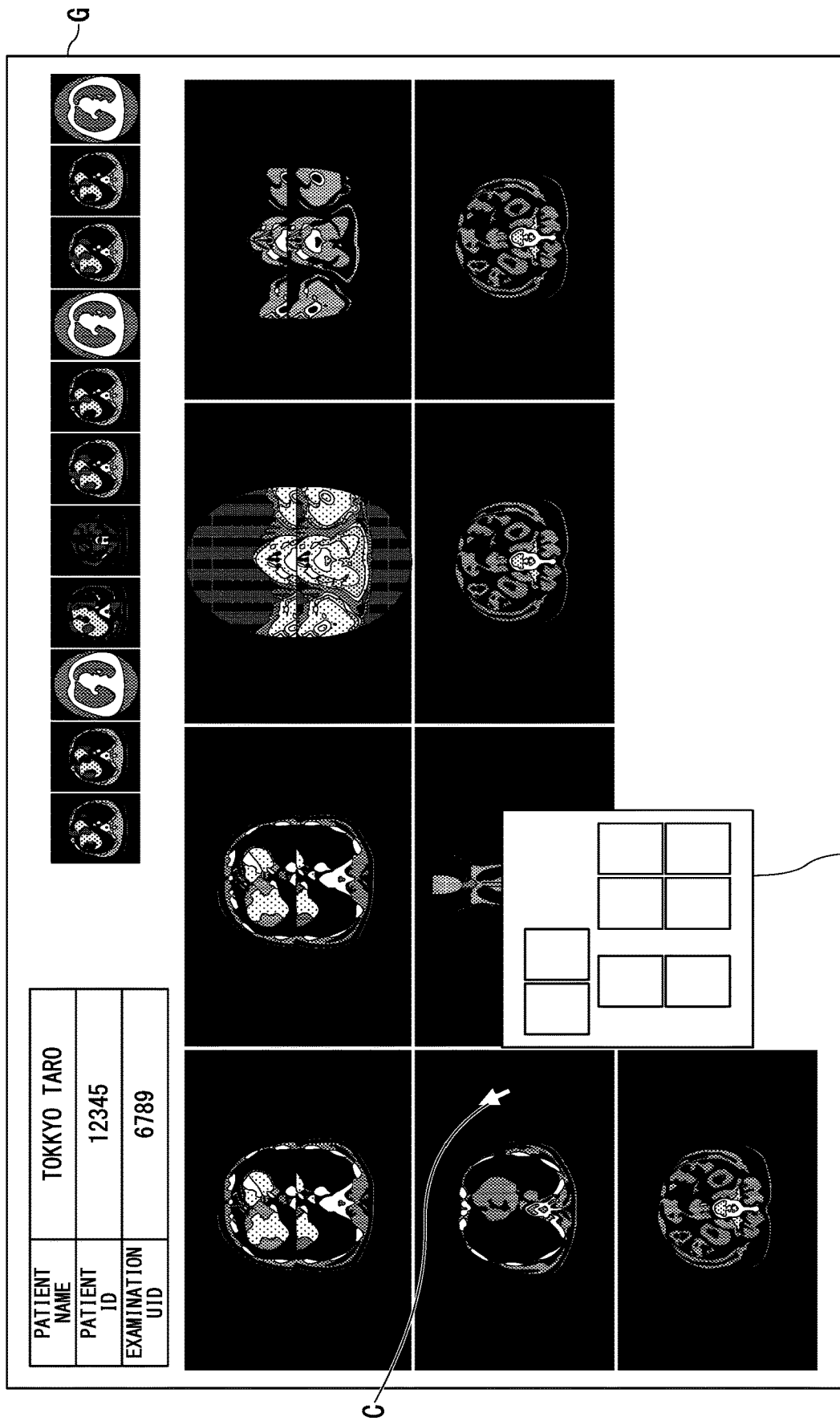
FIG. 8 is a schematic diagram illustrating a method of displaying choices of the display layout in the medical image display apparatus according to the first modification.

FIG. 8 is a schematic diagram illustrating a method of displaying choices of the display layout in the medical image display apparatus 10 according to the first modification. FIG. 8 shows the same layout of the display screen G as that in FIG. 3.

As shown in FIG. 8, choices of the display layout are displayed in the second pop-up menu M2 near the interpretation-target image data (partially overlaid with the mouse cursor C) which are specified among the plurality of interpretation-target image data. FIG. 8 shows three choices of the display layout including: parallel display of two images in horizontal arrangement (i.e., 1 row and 2 columns); parallel display of two images in vertical arrangement (i.e., 1 column and 2 rows); and parallel display of four images arranged in a square (i.e., two columns and two rows).

The determination function 113 continuously detects the mouse cursor C on the display screen G and determines that it is superimposed when the detected mouse cursor C is superimposed on the display range of the interpretation-target image data (FIG. 8). Additionally, the determination function 113 may continuously detect the mouse cursor C and determine that it is superimposed when (i) the detected mouse cursor C is located in the display range of the interpretation-target image data (for example, overlaid with the button icon within the display range) and (ii) a selection instruction via the input interface 13 (performed by single or double click of the mouse button or click of the icon, for example) is also received. Although the three display layouts are shown in FIG. 8 including three parallel-display patterns of: two images in horizontal arrangement; two images in vertical arrangement; and four images arranged in a square, the aspects of the display layout are not limited to such an aspect. The operator can readily select a desired display layout from the plurality of choices of the display layout shown in the second pop-up menu M2.

Subsequent to the determination of the comparative image data in the step ST5 of FIG. 4, the fixing function 115 determines at least one display layout, as selected via the mouse cursor C, among the choices shown in the second pop-up menu M2. The second display control function 114 arranges (i.e., allocates) the comparative image data determined in the step ST5 of FIG. 4 and the specified interpretation-target image data in the determined display layout (for example, parallel display of two images in horizontal arrangement) for display. The determination of the comparative image data and the display layout can be made in any order.

The second display control function 114 may be configured to switch between the display screen for determining the comparative image data (shown in FIG. 5 and FIG. 6) and the display screen for determining the display layout by switching tabs.

Since the medical image display apparatus 10 eliminates the need to select the comparative image data from the thumbnail field R3, the image display of the thumbnail field R3 in FIG. 8 can be omitted.

According to the first modification of the medical image display apparatus 10 described above, in addition to the above-described effects available by the medical image display apparatus 10, efficiency in selecting the display layout of the interpretation-target image data and the corresponding comparative image data can be improved.

Second Modification

The medical image display apparatus 10 may be configured to simultaneously select the comparative image data and its display layout. In this case, the second display control function 114 displays the plurality of choices of the comparative image data which are shown in the plurality of choices of the display layout in the pop-up menu (i.e., third pop-up menu described below) in the interpretation adjacent region. Further, the fixing function 115 determines (i.e., fixes) the display layout, as selected via the mouse cursor C, from the plurality of choices presented in the third pop-up menu, and then determines (i.e., fixes) one or more comparative image data presented in this determined display layout.

Figure 9:
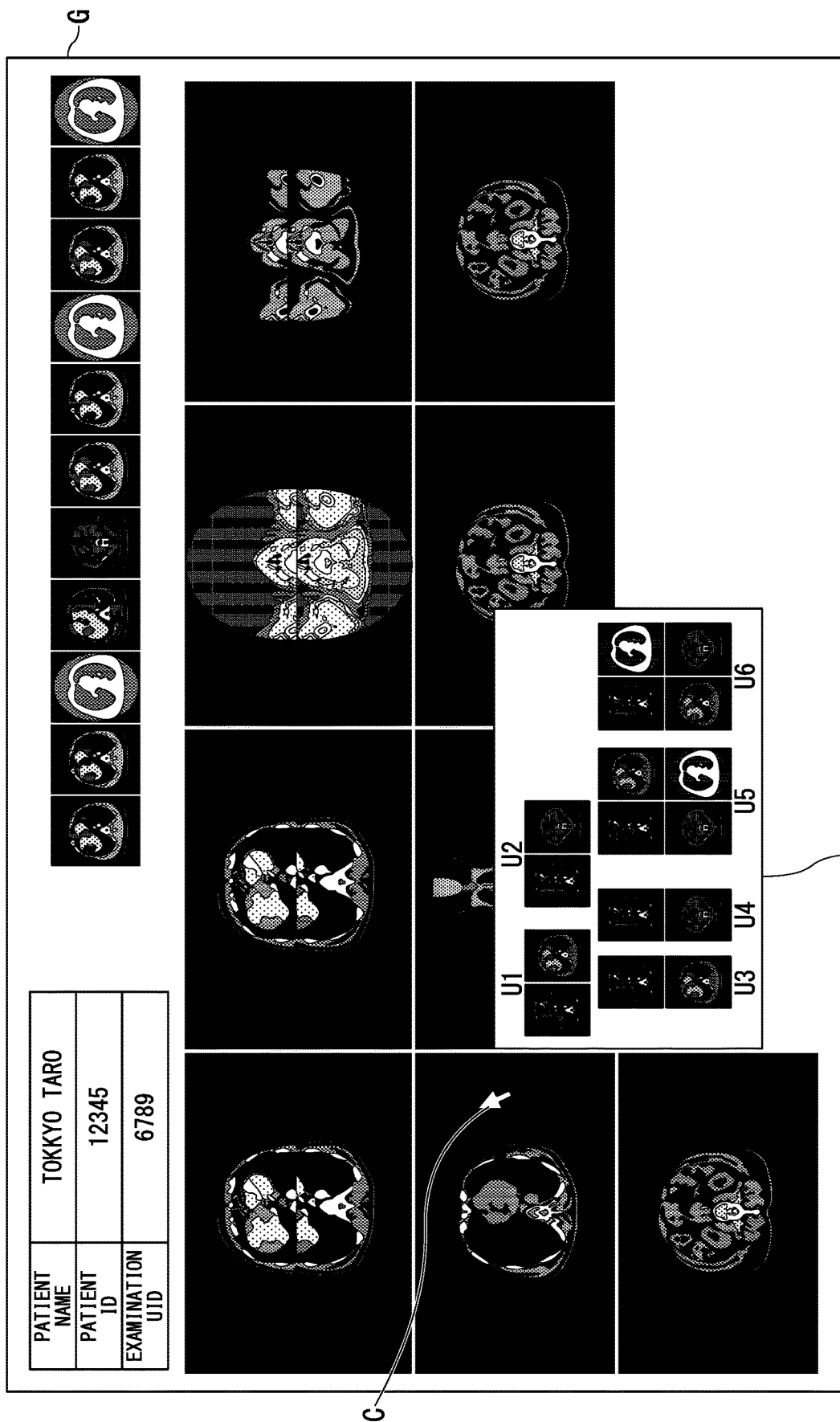
FIG. 9 is a schematic diagram illustrating a method of displaying choices of the display layout and choices of the comparative image data in the medical image display apparatus according to the second modification.

FIG. 9 is a schematic diagram illustrating a method of displaying choices of the display layout and choices of the comparative image data in the medical image display apparatus 10 according to the second modification. FIG. 9 shows the same layout of the display screen G as that in FIG. 3.

As shown in FIG. 9, near the interpretation-target image data (partially overlaid with the mouse cursor C) which are specified among the plurality of interpretation-target image data, the choices of the comparative image data and the specified interpretation-target image data presented in the choices for display layout are displayed in the third pop-up menu M3. FIG. 9 shows an aspect in which the choices of the comparative image data are presented in the choices of the display layout including three parallel-display patterns of two images in horizontal arrangement, two images in vertical arrangement, and four images being arranged in a square. The display layout is not limited to the above-described three patterns, as long as one or more interpretation-target image data and one or more choices of the comparative image data are presented in the display layout.

In the case of the choices of the display layout having parallel-display patterns including two images in horizontal arrangement as well as in vertical arrangement, one specified interpretation-target image datum and one choice of the comparative image data are arranged in the choices of the display layout. For example, the third pop-up menu M3 shown in FIG. 9 includes: choices U1 and U2 where two images are arranged in parallel in horizontal arrangement; and choices U3 and U4 where two images are arranged in parallel in vertical arrangement.

In the choice U1 of the display layout, one specified interpretation-target image datum is displayed on the left side and one choice of the comparative image data (i.e., first comparative image data) is displayed on the right side.

In the choice U2 of the display layout, one specified interpretation-target image datum is displayed on the left side and one choice of the comparative image data (i.e., second comparative image data) is displayed on the right side.

In the choice U3 of the display layout, one specified interpretation-target image datum is displayed on the upper side and one choice for the first comparative image data is displayed on the lower side.

In the choice U4 of the display layout, one specified interpretation-target image datum is displayed on the upper side and one choice for the second comparative image data is displayed on the lower side.

In the case of the display layout where four images are arranged in a square, one specified interpretation-target image datum and three choices for the comparative image data are arranged in the display layout. For example, the third pop-up menu M3 shown in FIG. 9 includes choices U5 and U6 of the display layout where four images are arranged in a square.

In the choice U5 of the display layout, one specified interpretation-target image datum is displayed in the upper left corner and three choices of the comparative image data (i.e., first to third comparative image data) are displayed in the remaining ¾ region.

In the choice U6 of the display layout, one specified interpretation-target image datum is displayed in the upper left corner and three choices of the comparative image data (i.e., fourth to sixth comparative image data) are displayed in the remaining ¾ region.

In the case of the display layout where four images are arranged in a square, a plurality of (for example, two) specified interpretation-target image data and a plurality of (for example, two) choices of the comparative image data may be arranged in the display layout. In this case, the plurality of specified interpretation-target image data include: the interpretation-target image data on which the mouse cursor C is superimposed; and the interpretation-target image data that are designated in advance by following a selection instruction (for example, single or double click of the mouse button or click of the icon) via the input interface 13.

The determination function 113 continuously detects the mouse cursor C on the display screen, and determines that it is superimposed when the detected mouse cursor C is located in the display range of the interpretation-target image data (FIG. 9). Additionally, the determination function 113 may continuously detect the mouse cursor C and determine that it is superimposed when (i) the detected the mouse cursor C is superimposed on the display range (for example, overlaid with the button icon within the display range) of the interpretation-target image data and (ii) a selection instruction via the input interface 13 (performed by single or double click of the mouse button or click of the icon, for example). The operator can readily select a desired display layout and desired comparative image data at the same time from the plurality of choices of the display layout shown in the third pop-up menu M3.

In the medical image display apparatus 10, it is not necessary to select the comparative image data from the thumbnail field R3, and thus, the image display of the thumbnail field R3 in FIG. 9 can be omitted.

According to the second modification of the medical image display apparatus 10 described above, in addition to the above-described effects available by the medical image display apparatus 10, the operation related to display layout is simplified, and the efficiency in selecting the display layout for the interpretation-target image data and the corresponding comparative image data can be improved.

Third Modification

The second modification may be further modified in such a manner that a plurality of choices of the display layout and the comparative image data can be individually selected, and this aspect will be described as a third modification. In the pop-up menu (i.e., fourth pop-up menu described below) shown in the interpretation adjacent region, the second display control function 114 displays a plurality of choices of the display layout meant for displaying choices of the comparative image data, and a plurality of choices of the comparative image data. The fixing function 115 determines at least one comparative image data, as selected via the mouse cursor C, among the plurality of choices displayed in the fourth pop-up menu. Further, the fixing function 115 also determines at least one display layout, as selected via the mouse cursor C, among the plurality of choices displayed in the fourth pop-up menu.

Figure 10:
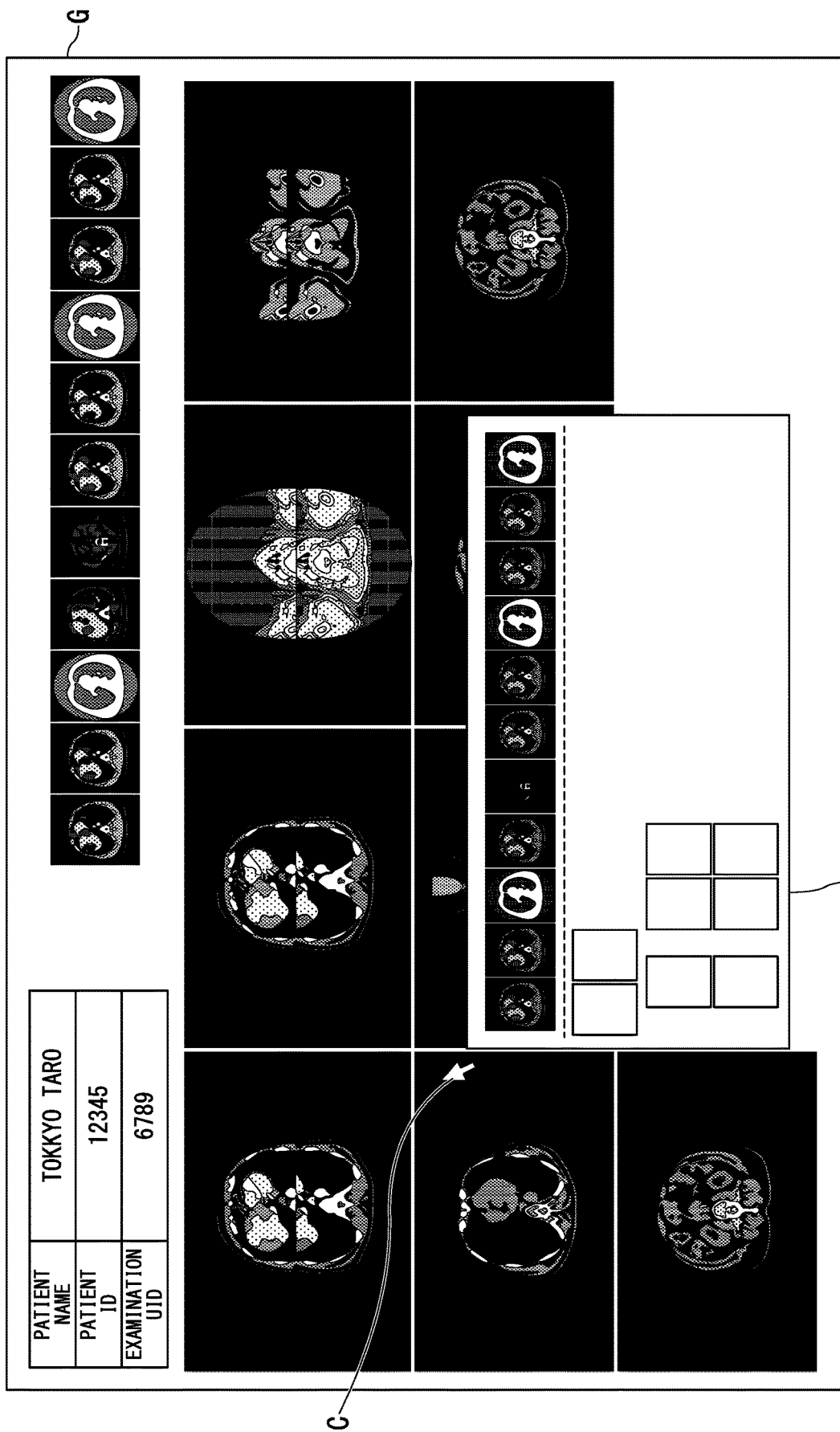
FIG. 10 is a schematic diagram illustrating a method of displaying choices of the display layout and choices of the comparative image data in the medical image display apparatus according to the third modification.
Figure 11:
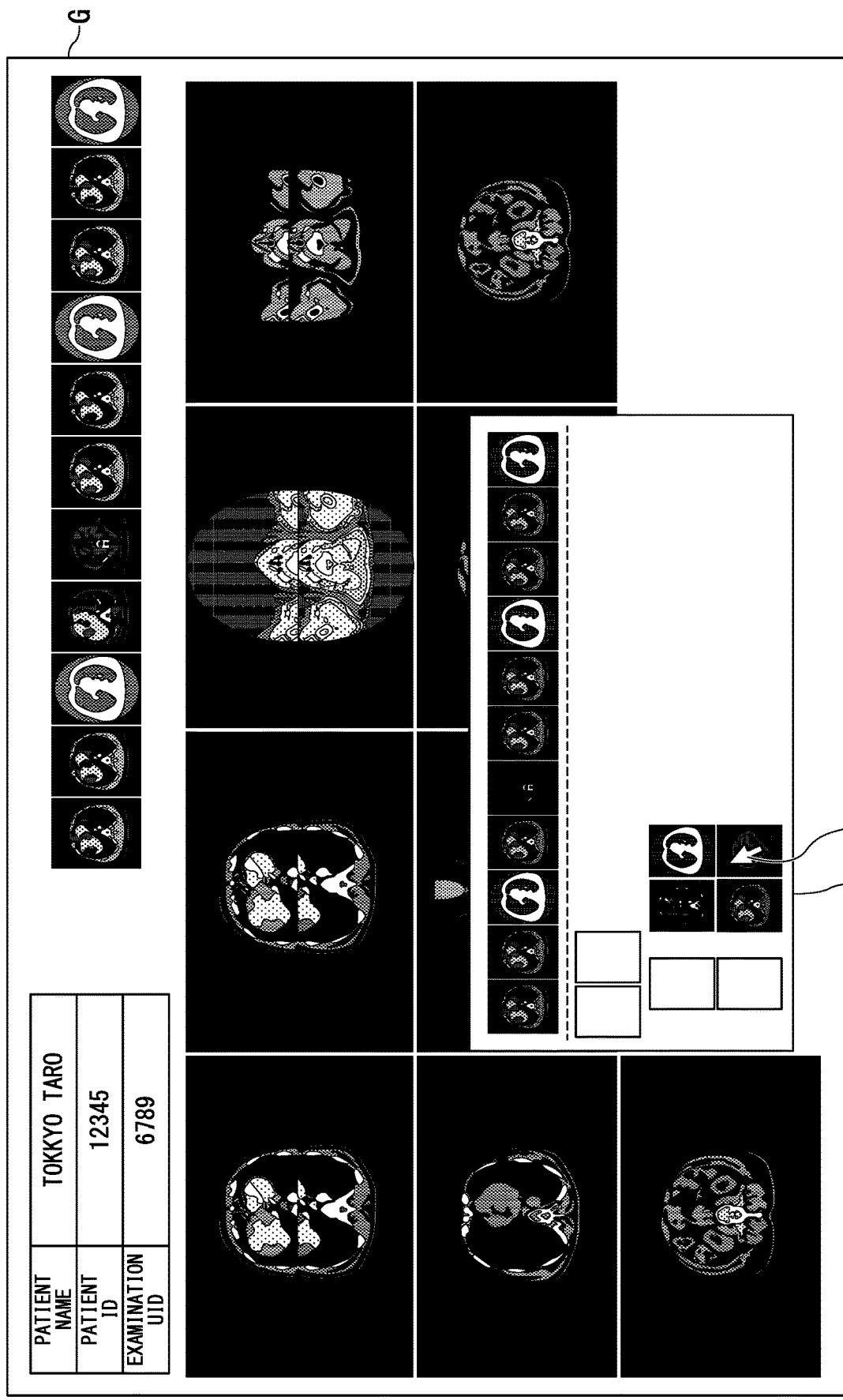
FIG. 11 is a schematic diagram illustrating a method of displaying choices of the display layout and choices of the comparative image data in the medical image display apparatus according to the third modification.

Each of FIG. 10 and FIG. 11 is a schematic diagram illustrating a method of displaying choices of the display layout and choices of the comparative image data in the medical image display apparatus 10 according to the third modification. each of FIG. 10 and FIG. 11 shows the same layout of the display screen G as t that in FIG. 3.

As shown in FIG. 10, near the interpretation-target image data (partially overlaid with the mouse cursor C) which are specified among the plurality of interpretation-target image data, choices of the comparative image data and choices of the display layout are shown in the fourth pop-up menu M4. Each of the plurality of choices of the comparative image data in the fourth pop-up menu M4 is displayed at a position closer to the specified interpretation-target image data (or the mouse cursor C) than the corresponding choices of the comparative image data shown in the thumbnail field E3. The plurality of choices of the comparative image data may be displayed in the shape of "U" or "L" or in rectangle around the specified interpretation-target image data or may be displayed so as to draw a rectangle over the top, bottom, right, and left of the specified interpretation-target image data. In the fourth pop-up menu M4 in FIG. 10, eleven choices of the comparative image data are arranged on the upper side, and three choices of the display layout are arranged on the lower side that include the three parallel-display patterns of: two images in horizontal arrangement; two images in vertical arrangement; and four images arranged in a square.

The determination function 113 continuously detects the mouse cursor C on the display screen, and determines that it is superimposed when the detected mouse cursor C is located in the display range of the interpretation-target image data (FIG. 10). Additionally, the determination function 113 may continuously detect the mouse cursor C and determine that it is superimposed when (i) the detected mouse cursor C is located in the display range (for example, overlaid with the button icon within the display range) of the interpretation-target image data and (ii) a selection instruction via the input interface 13 (performed by single or double click of the mouse button or click of the icon, for example) is received. The operator can readily select a desired display layout from the lower side of the fourth pop-up menu M4 and readily select desired comparative image data from the upper side of the fourth pop-up menu M4.

As shown in FIG. 11, the display aspect of the third modification may be configured such that the interpretation-target image data and the selected comparative image data are arranged in selected the display layout among the three choices including the three parallel-display patterns (i.e., two images in horizontal arrangement, two images in vertical arrangement, and four images arranged in a square) displayed in the fourth pop-up menu M4. In this aspect, the operator can readily select desired comparative image data and a desired display layout by moving the desired comparative image data among the plurality of choices shown in the fourth pop-up menu M4 into the desired display layout among the three choices. For example, as shown in FIG. 11, the operator uses the mouse cursor C on the display screen to move (for example, drag and drop) the desired comparative image data into the desired display layout where four images are arranged in a square.

Since the medical image display apparatus 10 eliminates the need to select the comparative image data from the thumbnail field R3, the image display in the thumbnail field R3 in FIG. 10 and FIG. 11 can be omitted.

According to the third modification of the medical image display apparatus 10 described above, in addition to the above-described effects available by the medical image display apparatus 10, operation related to display layout can be reduced, and thus, efficiency in selecting the display layout of the interpretation-target image data and the corresponding comparative image data can be improved.

Fourth Modification

Figure 12:
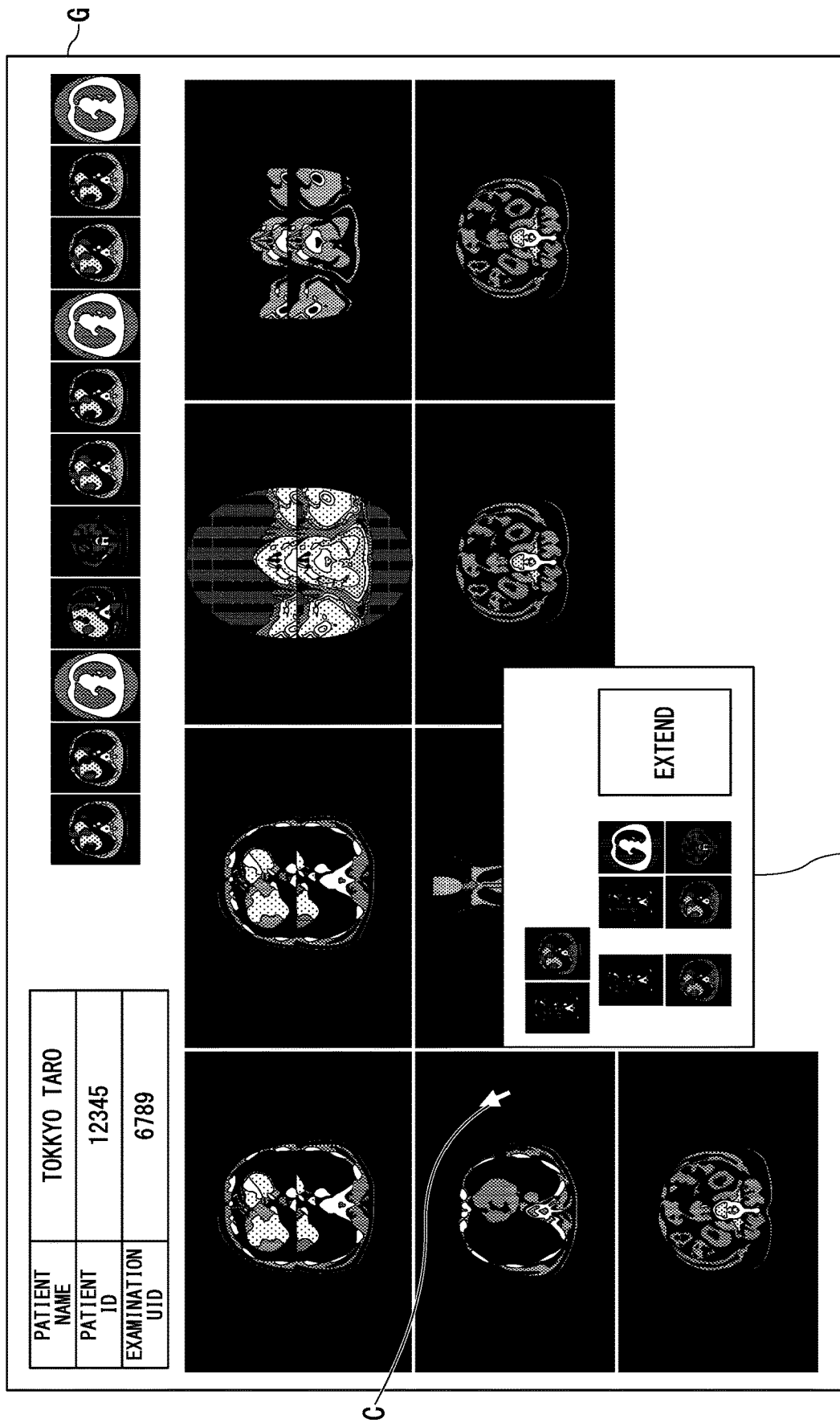
FIG. 12 is a schematic diagram illustrating a method of displaying choices of the display layout and choices of the comparative image data in the medical image display apparatus according to the fourth modification.

The methods of selecting and determining the display layout has been described in the first to third modifications. There are a wide variety of display layouts, and it is difficult to display all of the display layouts as pull-down menus. Thus, the second display control function 114 initially displays only the display layout(s) with higher priority in the pull-down menu while supplementarily displaying the display layout(s) with lower priority by using the extension function of the pull-down menu (FIG. 12). The display layout(s) with lower priority may be displayed by extended operation such as long-press, click, and/or double-click of the mouse button, or by click of the right (or left) mouse button, or by pressing a GUI such as an icon on the display screen. The order of priority may be determined for each medical institution (for example, hospital) or may be determined for each operator.

The second display control function 114 may determine or derive the priority order from past usage history. In this case, the second display control function 114 determines the display layout based on the operator (or the medical institution). This determination processing may be performed by using, for example, a lookup table (LUT) in which the identification information of each operator is associated with usage history of display layouts. In this processing, machine learning such as deep learning using a multilayer neural network like a CNN (Convolutional Neural Network) and a CDBN (Convolutional Deep Belief Network) may be used.

FIG. 12 is a schematic diagram illustrating a method of displaying choices of the display layout and choices of the comparative image data in the medical image display apparatus 10 according to the fourth modification. Although FIG. 12 illustrates a modification of the embodiment in FIG. 9, the aspect shown in FIG. 12 can also be applied to the respective aspects shown in FIG. 8, FIG. 10, and FIG. 11. FIG. 12 shows the same layout of the display screen G as that in FIG. 3.

As shown in FIG. 12, near the interpretation-target image data (partially overlaid with the mouse cursor C) which are specified among the plurality of interpretation-target image data, a fifth pop-up menu M5 is displayed. In the fifth pop-up menu M5, the interpretation-target image data and choices of the comparative image data are arranged in each choice of the display layout. Each of the plurality of choices of the comparative image data presented in the fifth pop-up menu M5 is displayed at a position closer to the specified interpretation-target image data (or the mouse cursor C) than the choices of the corresponding comparative image data shown in the thumbnail field R3. FIG. 12 shows an aspect in which the interpretation-target image data and the choice(s) of the comparative image data are arranged in each of the three choices of the display layout including the three parallel-display patterns of: two images in horizontal arrangement; two images in vertical arrangement; and four images arranged in a square. The fifth pop-up menu M5 includes an extend button icon. The display layouts that are excluded from the initial displayed choices can be sequentially available when the operator clicks the extend button icon shown in the fifth pop-up menu M5, and then, the operator can readily select a desired display layout.

Since the medical image display apparatus 10 eliminates the need to select the comparative image data from the thumbnail field R3, the image display of the thumbnail field R3 in FIG. 12 can be omitted.

According to the fourth modification of the medical image display apparatus 10 described above, in addition to the above-described effects available by the medical image display apparatus 10, the operation related to display layout can be reduced, and thus, efficiency in selecting the display layout of the interpretation-target image data and the corresponding comparative image data can be improved.

(Method of Specifying Choices of Comparative Image Data)

The acquisition function 111 searches and retrieves the choices of the comparative image data on the basis of: (1) usage status of the operator (for example, an operator and a medical institution); (2) peculiarities of the interpretation-target image data; (3) peculiarities of the medical image data to be specified (choices of comparative image data); and (4) user settings.

(1) Usage Status of the Operator

The acquisition function 111 searches and acquires choices of the comparative image data on the basis of the usage status of the operator. The acquisition function 111 acquires choices of the comparative image data with higher priority. The priority may be determined for each medical institution (for example, hospital) or may be determined for each operator.

The acquisition function 111 may determine or derive the priority order from past usage history. In this case, the acquisition function 111 determines choices of the comparative image data based on the operator (or the medical institution). This determination processing may be performed by using, for example, a lookup table in which the identification information of each operator is associated with the choices of the comparative image data. In this processing, the machine learning such as the above-described deep learning using a multilayer neural network like a CNN and a CDBN may be used. In addition to the identification information of each operator, as input data for the learning model, by adding information stored as supplementary information of DICOM such as an examination purpose, a type of medical image diagnostic apparatus, an examination site, a study description, a series description, and a protocol, highly accurate output data can be obtained.

(2) Peculiarities of Interpretation-Target Image Data

The acquisition function 111 acquires medical image data as choices of the comparative image data, from a medical image diagnostic apparatus that is the same or similar to the apparatus having acquired the interpretation-target image data. Whether the medical image diagnostic apparatuses for acquiring the interpreted image data and the choices of the comparative image data are of similar type or not can be determined based on their model names. This processing may also be performed by using, for example, a lookup table in which the type of medical image diagnostic apparatus having acquired the interpretation-target image data is associated with similar types of medical image diagnostic apparatuses. In this processing, the machine learning such as the above-described deep learning using a multilayer neural network like a CNN and a CDBN may be used.

Similarly, as the choice(s) of the comparative image data, the acquisition function 111 acquires the medical image data which are the same as or similar to the interpretation-target image data in terms of examination site and/or examination purpose. Similar examination sites include: any anatomical site that can be referred to the site shown in interpretation-target image data; any anatomical site that partially match, for example, the front or back part of the site shown in interpretation-target image data; any anatomical landmark that is similar to the anatomical landmark shown in the interpretation-target image data (for example, the chest is included in the whole body, and thus, both are considered having similar anatomical landmarks); and any site having possibility of metastasis from the site shown in interpretation-target image data.

As choices of the comparative image data, the acquisition function 111 also acquires the medical image data which are the same as or similar to the interpretation-target image data in terms of imaging direction (for example, axial, sagittal, and coronal cross-sections). Whether the imaging directions of both the interpretation-target image data and the choice of the comparative image data are similar or not can be determined by acquiring the imaging directions of both images. This processing may be performed by using, for example, a lookup table in which the imaging direction of the interpretation-target image data are associated with similar imaging directions. In this processing, the machine learning such as the above-described deep learning using a multilayer neural network like a CNN and a CDBN may be used.

Similarly, when the interpretation-target image data are acquired in a contrast-enhanced examination, the acquisition function 111 acquires medical image data in both a contrast-enhanced examination and a non-contrast-enhanced examination as choices of the comparative image data. When the interpretation-target image data are CT image data, the acquisition function 111 acquires CT image data having been subjected to special reconstruction processing as choices of the comparative image data. When the interpretation-target image data are MR image data, the acquisition function 111 acquires MR image data generated by a specific protocol as choices of the comparative image data.

(3) Peculiarities of Medical Image Data to be Specified (Choices of Comparative Image Data)

Regardless of the type of interpretation-target image data, as choices of the comparative image data, the acquisition function 111 acquires: medical image data generated under special conditions (for example, medical image data excluding those defined by a hanging protocol, medical image data that are not usually generated, and/or medical image data with a caution mark); medical image data equivalent to enlarged images (based on a series description); a key image used in the previous examination; medical image data with measurement and annotation; and medical image data to be followed (detected from electronic medical records). As choices of the comparative image data, the acquisition function 111 can also acquire medical image data within a fixed period (which is determined on the basis of, for example, user settings and/or medical judgment that may exclude a post-treatment span and/or forcibly include a risky span).

(4) User Settings

Regardless of the type of interpretation-target image data, the acquisition function 111 acquires medical image data of at least one region (for example, an anatomical site that is easily overlooked depending on skills of each operator) designated by an operator or a medical institution as the choice(s) of the comparative image data.

According to at least one embodiment described above, efficiency in selecting the comparative image data corresponding to the interpretation-target image data can be improved.

While certain embodiments have been described, these embodiments have been presented by way of example only, and are not intended to limit the scope of the inventions. Indeed, the novel methods and systems described herein may be embodied in a variety of other forms; furthermore, various omissions, substitutions, changes, and combinations of embodiments in the form of the methods and systems described herein may be made without departing from the spirit of the inventions. The accompanying claims and their equivalents are intended to cover such forms or modifications as would fall within the scope and spirit of the inventions.

What is claimed is:

1. A medical image display apparatus comprising:
   processing circuitry configured to
   determine whether a mouse cursor is superimposed on a display range of interpretation-target medical image data in a display screen of a display or not,
   display, when the mouse cursor is determined to be superimposed on the display range, both of the interpretation-target medical image data and at least one choice of comparative medical image data corresponding to interpretation-target medical image data, specified by a position of a mouse cursor, arranged in choices of display layout in a pop-up menu to be shown in an interpretation adjacent region where the specified interpretation-target medical image data is not superimposed and is adjacent to the specified interpretation-target medical image data,
   determine a display layout as selected via the mouse cursor among choices presented in the pop-up menu, and
   determine a choice of comparative medical image data arranged in the determined display layout as the comparative medical image data for comparison.

2. The medical image display apparatus according to claim 1, wherein the processing circuitry is configured to
   initially display at least one choice of display layout having higher priority among choices presented in a pull-down menu, and
   supplementarily display at least one choice of display layout having lower priority among choices presented in the pull-down menu by using an extended function.

3. A medical image display system comprising:
   a medical image display apparatus; and
   a medical image management apparatus, wherein
   the medical image display apparatus and the medical image management apparatus are interconnected via a network and configured to communicate with each other, and
   the medical image display apparatus comprises processing circuitry configured to
   acquire medical image data from the medical image management apparatus,
   determine whether a mouse cursor is superimposed on a display range of interpretation-target medical image data in a display screen of a display or not,
   display, when the mouse cursor is determined to be superimposed on the display range, both of the interpretation-target medical image data and at least one choice of comparative medical image data corresponding to interpretation-target medical image data, specified by a position of a mouse cursor, arranged in choices of display layout in a pop-up menu to be shown in an interpretation adjacent region where the specified interpretation-target medical image data is not superimposed and is adjacent to the specified interpretation-target medical image data,
   determine a display layout as selected via the mouse cursor among choices presented in the pop-up menu, and
   determine a choice of comparative medical image data arranged in the determined display layout as the comparative medical image data for comparison.

4. A medical image display method comprising:
   determining, by processing circuitry, whether a mouse cursor is superimposed on a display range of interpretation-target medical image data in a display screen of a display or not;
   displaying, by the processing circuitry, when the mouse cursor is determined to be superimposed on the display range, both of the interpretation-target medical image data and at least one choice of comparative medical image data corresponding to interpretation-target medical image data, specified by a position of a mouse cursor, arranged in choices of display layout in a pop-up menu to be shown in an interpretation adjacent region where the specified interpretation-target medical image data is not superimposed and is adjacent to the specified interpretation-target medical image data;

determining, by the processing circuitry, a display layout as selected via the mouse cursor among choices presented in the pop-up menu; and determining, by the processing circuitry, a choice of comparative medical image data arranged in the determined display layout as the comparative medical image data for comparison.

* * * * *